United States Patent [19]

Sheldon et al.

[11] Patent Number: 4,656,309

[45] Date of Patent: Apr. 7, 1987

[54] PREPARATION OF ALPHA-PIVALOYL-SUBSTITUTED ACETIC ACID ESTERS

[75] Inventors: Roger A. Sheldon; Hendricus J. Heijmen, both of Amsterdam, Netherlands

[73] Assignee: Shell Oil Company, Houston, Tex.

[21] Appl. No.: 316,200

[22] Filed: Oct. 29, 1981

[30] Foreign Application Priority Data

Nov. 7, 1980 [GB] United Kingdom ............... 8035846

[51] Int. Cl.$^4$ .......................................... C07C 69/716
[52] U.S. Cl. ................................................... 560/174
[58] Field of Search ............................... 560/174, 145

[56] References Cited

U.S. PATENT DOCUMENTS 3,518,296  6/1970  Bucourt et al. ............... 560/174
3,577,455  5/1971  Jones et al. ................... 560/174
3,798,259  3/1974  Wehrli ........................... 560/174

Primary Examiner—Werren B. Lone

[57] ABSTRACT

An alpha-pivaloyl-substituted acetic acid ester of the formula $(H_3C)_3CCOCH_2COOR$, wherein R is an optionally-substituted alkyl, aryl, alkaryl, or aralkyl group, is prepared by (a) reacting an alpha-pivaloyl-substituted malonic acid ester with a base selected from the class consisting of alkali metal alkoxides and compounds of the formula MXY, wherein M is an alkaline earth metal, X is an alkoxy group, and Y is either an alkoxy group or a halogen atom, and (b) acidifying the resulting reaction mixture.

10 Claims, No Drawings

PREPARATION OF ALPHA-PIVALOYL-SUBSTITUTED ACETIC ACID ESTERS

BACKGROUND OF THE INVENTION

The present invention relates to a process for the preparation of alpha-pivaloyl-substituted acetic acid esters.

The alpha-pivaloyl-substituted acetic acid esters which may be prepared by practice of the process of the invention are known compounds having utility as photographic chemicals and as pharmaceutical intermediates. Particular examples of these compounds are methyl pivaloylacetate disclosed in French Pat. No. 2,191,887, in British Pat. Nos. 1,483,948 and 1,491,606, and in a publication by F. W. Swamer and C. R. Hauser (J. Amer. Chem. Soc., 72 (1950), 1352), and ethyl pivaloylacetate disclosed in U.S. Pat. No. 3,142,692.

Several routes are known in the art for production of sterically hindered aliphatic beta-keto esters, such as the alpha-pivaloyl acetic acid esters. Generally, the yields of desired product are low under known synthesis procedures, a result of the formation of a variety of side products. Steps which can be taken to improve the yields of conventional processes are commercially impractical, because they require the use of expense reagents and/or solvents.

The present invention particularly relates to a preparation of alpha-pivaloyl-substituted acetic acid esters in which pivaloyl malonic acid esters are subjected to reaction with specific bases and the reaction product subsequently acidified. It is considered surprising that this route can be readily followed to prepare the alpha-pivaloyl-substituted acetic acid esters, since acyl malonic acid esters are known to undergo rapid deacylation in base-catalyzed reactions to give acids in high yield (Cahiers de Synthese Organique, Vol. V (1959), p.254) and also to degrade to corresponding ketones when treated with acid (Ibid, p.63). By means of the process of the invention, however, it is found to be possible to cleave the pivaloyl malonic ester, replacing one of its two ester moieties with hydrogen, while maintaining the pivaloyl moiety and one ester moiety in the same molecule.

SUMMARY OF THE INVENTION

The present invention is a process for the preparation of alpha-pivaloyl-substituted acetic acid esters, which comprises reacting a pivaloyl malonic ester of the formula

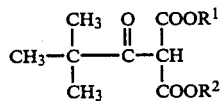

wherein $R^1$ and $R^2$ each individually represents an optionally substituted alkyl, aryl, alkaryl, or aralkyl group, with a base selected from the group consisting of alkali metal alkoxides and compounds of the formula MXY wherein M is an alkaline earth metal, X is an alkoxy group, and Y is either an alkoxy group or a halogen atom, and acidifying the resulting reaction mixture.

DESCRIPTION OF THE PREFERRED EMBODIMENTS

The invention is advantageously applied for the preparation of the class of alpha-pivaloyl-substituted acetic acid esters of the formula $(H_3C)_3CCOCH_2COOR$ wherein R is an optionally substituted alkyl, aryl, alkaryl, or aralkyl group. It will be understood that these ester products also comprise the corresponding enol compounds, since beta-keto esters normally exhibit keto-enol tautomerism. The equilibrium composition in the keto-enol mixture depends on such factors as temperature and the presence of solvents and other compounds in the mixture.

The class of alpha-pivaloyl malonic acid esters suitable as starting materials in the process of the invention is defined in terms of the $R^1$ and $R^2$ groups, which may be the same or different, and which individually represent an optionally substituted alkyl, aryl, alkaryl, or aralkyl group. In most cases, a starting material in which $R^1$ and $R^2$ are the same will be preferred, so that the invention will yield a product having the same R group in the ester molecules rather than one containing a mixture of molecules with different R groups. Halogen atoms and alkoxy groups are preferred as the optional substituents. Substitution of the alkyl, aryl, alkaryl or aralkyl group by other substituents essentially inert under processing conditions is, however, also suitable. Preferred are $R^1$ and $R^2$ groups having up to 10 carbon atoms. Alkyl groups are particularly preferred, while alkyl groups of up to 5 carbon atoms are still more preferred. Most preferred are methyl and ethyl groups.

The starting alpha-pivaloyl malonic esters are known in the art. In a preferred method for their preparation pivaloylation of a malonic acid ester (a dialkyl malonate of the formula $R^1OOCCH_2COOR^2$) is achieved by converting the ester to the corresponding metal-diester salt and subsequently reacting the salt with a pivaloyl halide. As an example, the ester may be reacted with one equivalent of sodium metal, sodium hydride, or, preferably, sodium alkoxide to prepare the sodio malonic acid diester. Other metals (for instance, magnesium) and their compounds are also suitable for formation of the metal-diester salt. This reaction is preferably carried out at a temperature in the range of about 10° to 40° C. and in the presence of a solvent. As suitable pivaloylation solvents, mention may be made of ethers, such as diethyl ether, diisopropyl ether, di-sec-butyl ether, di-n-butyl ether, and 1,2-dimethoxyethane, of aromatic hydrocarbons, such as benzene, toluene and the xylenes, and of cycloalkanes, such as cyclohexane. Typically, good results can be obtained by adding a solution of the metal compound (for instance, a 30% solution of sodium methoxide in methanol) to a stirred solution of the malonic acid ester in a solvent, and evaporating the methanol to leave a slurry of the metal-diester salt. A pivaloyl halide, e.g., pivaloyl chloride, may be added directly to this slurry, preferably under stirring and at ambient or slightly higher temperature, to form the alpha-pivaloyl malonic ester. It has been observed that the pivaloylation reaction may also result in formation of an undesirable amount of di-pivaloyl compounds. The use of a polar pivaloylation solvent is found to reduce this formation, as is the use of a lower ketone as a co-solvent, for example, acetone in an amount of about 20% by weight based on total solvent. Di-pivaloyl formation can also be reduced through the use of a large excess, e.g., a ten-fold molar excess, of the malonic acid ester.

For purposes of the present invention, the alpha-pivaloyl malonic ester starting material may be suitably derived by procedures other than those described above. However, preference is stated for these procedures because, when they are applied for synthesis of the ester starting material, it is not necessary to isolate the alpha-pivaloyl malonic ester from the pivaloylation reaction mixture before its use in the invention. If it is desired, isolation of the alpha-pivaloyl malonic acid ester from the pivaloylation reaction mixture can, of course, be accomplished prior to practice of the invention, for instance, by filtering the reaction mixture to remove solid salts and distilling to remove solvent.

Suitable bases to be used in the process according to the present invention comprise the alkoxides of Group I metals as well as alkoxides and/or mixed alkoxides-halides of Group II metals. Preference is given to the use of alkali metal alkoxides, particularly sodium or potassium alkoxides, and most particularly sodium methoxide and sodium ethoxide. The alkoxy group or groups preferably have less than six carbon atoms, most preferably less than three carbon atoms. For a Group II metal-containing base, the alkoxide of formula MXY wherein both X and Y represent alkoxy groups is preferred over the mixed alkoxide-halide wherein X is alkoxy and Y is a halogen atom. The specified class of bases is critical to the success of the process of the invention. As referred to hereinbefore, the use of other common bases such as sodium hydroxide, instead of those specified, leads to formation of a large amount of pivalic acid, the result of an undesired acyl-cleavage of the starting material. As an example, when triethylamine is applied as a base only low conversions (about 20%) are observed and the desired alpha-pivaloyl acetic acid esters are produced in negligible quantities (about 1%). The base and the alpha-pivaloyl malonic acid ester starting material are most preferably used in approximately equimolar quantities, although the ratio of these reactants can suitably vary. A slight excess of the base (e.g., up to 20 percent by mol) is, for instance, suitable. Preferably, the molar ratio of base to alpha-pivaloyl malonic acid ester is between about 0.8 and 1.2, while a ratio between about 0.9 and 1.1 is considered more preferred.

Reaction between the alpha-pivaloyl malonic acid ester and the base for purposes of the invention is preferably carried out in an organic solvent. Examples of suitable solvents include aromatic hydrocarbons, such as benzene, toluene and the xylenes, as well as mixtures of aromatic hydrocarbons, cycloalkanes, such as cyclohexane, and dialkylethers such as di-isopropyl ether, di-n-butyl ether, and di-sec-butyl ether. An excess, by weight, of solvent over reactants is preferred, although the actual quantity of solvent used can vary widely. For convenience, a quantity of solvent no greater than fifty times, by weight, of that of the reactants is preferred, while particular preference is given to a quantity of solvent between 2 and 20 times that of the reactants. The base is preferably added to the reaction mixture in a dry, most preferably, dry powdered form, although solutions of base in a solvent, e.g., methanol or ethanol, are also suitable.

The process of the invention necessarily comprises the reaction of the alpha-pivaloyl malonic acid ester with the specified base, as well as the acidification of the resulting reaction mixture, and optionally further includes steps for production of the alpha-pivaloyl malinic acid ester by pivaloylation of the corresponding malonic acid ester. In either case, all of the steps involve liquid phase reactions, and the process can be conducted in a single reaction vessel. If the pivaloylation procedures are part of the overall process, it is very convenient to use the same base for formation of the metallo malonic acid ester as is used for reaction with the alpha-pivaloyl malonic acid ester to yield the desired product. Best results in an integrated process using a single solvent may be expected for a solvent of medium polarity. As indicated hereinabove, a polar solvent is preferred during pivaloylation and a non-polar solvent is preferred for best conversion of alpha-pivaloyl malonic acid ester to alpha-pivaloyl acetic acid ester. For an overall process including both such reactions, a single solvent of medium polarity, for example, a dialkyl ether, such as di-sec-butyl ether and di-n-butyl ether, or a cycloalkane, particularly a mixture of cyclohexane and acetone, can suitably be used as an acceptable compromise.

Both of the process steps, involving reaction of the alpha-pivaloyl malonic acid ester with the base and acidification of the resulting mixture, can suitably be carried out at ambient or higher temperatures. Preference is given to temperatures of 15° to 100° C., while process temperatures in the range of 35° to 75° C. are particularly preferred.

Following reaction of the specified base with the alpha-pivaloyl malonic acid ester, the mixture obtained is necessarily acidified to recover desired product. For acidification, the reaction mixture is treated with an acid, preferably an inorganic acid, more preferably an acid selected from the group consisting of hydrogen halides (particularly hydrochloric acid). Sufficient acid is added to bring the mixture to acidic pH (as measured in an aqueous extract of the mixture). Dilute acids are preferred, especially aqueous acid solutions. Treatment with an aqueous acid provides a two-phase system. The organic phase may be easily separated from the aqueous phase and subsequently dried to remove water, for instance, by treatment with an anhydrous salt drying agent such as magnesium sulfate.

Further treatment of the organic phase, for example, evaporation of the solvent and distillation (under reduced pressure), can be carried out to recover a purified alpha-pivaloyl acetic acid ester product.

The invention will now be illustrated by the following Examples and Comparative Examples.

EXAMPLE 1

A solution of dimethyl pivaloylmalonate (10.89 g, 50 mmols) in 100 ml di-sec-butyl ether was added to solid sodium methoxide (2.79 g, 50 mmols). The mixture was stirred at 50° C. for 5 hours, then allowed to cool and acidified with dilute hydrochloric acid. The organic phase was separated and dried over anhydrous magnesium sulfate. Analysis by gas-liquid chromatography (GLC), using tetramethylsilane (TMS) as an internal standard, indicated a yield of the methyl pivaloylacetate (alpha-pivaloyl acetic acid methyl ester) of 93% (calculated on 100% conversion of starting material). The remaining 7% was found to be methylpivalate.

EXAMPLE 2

The procedures of Example 1 were repeated using 100 ml of toluene as the solvent in place of the di-sec-butyl ether. Yield of methyl pivaloylacetate (all starting material converted) was 90%, the remaining 10% being pivalate.

EXAMPLE 3

The experiment of Example 1 was repeated using diethyl pivaloylmalonate as the starting material, instead of dimethyl pivaloylmalonate, and using diethyl ether as the solvent. The reaction was carried out at 35° C. for 7 hours. From GLC-analysis it appeared that conversion of starting material was essentially complete and that ethyl pivaloylacetate had been obtained in a yield of 83%. A small amount of ethyl pivalate had been formed, together with diethyl malonate and pivalic acid.

COMPARATIVE EXAMPLE A

The procedures described in Example 3 were repeated using sodium hydroxide as the base instead of sodium methoxide. After two hours reaction at 35° C. only 25% of the starting material had been converted with a selectivity to ethyl pivaloylacetate of only 28%. The main product appeared to be pivalic acid (selectivity 58%).

COMPARATIVE EXAMPLE B

Again following the general procedures of Example 3, using ethanol as the solvent and triethylamine instead of sodium methoxide as the base, reaction for four hours at 80° C. converted 20% of the starting material, with an overall yield of ethyl pivaloylacetate of only about 1%, calculated on mols of starting material.

EXAMPLE 4

Ethyl pivaloylacetate was prepared from diethyl malonate in the following manner. Diethyl malonate (64 g, 0.4 mol) was dissolved in 350 ml of a mixture of xylene isomers. A solution of sodium ethoxide, prepared by dissolving sodium (9.66 g, 0.42 g at) in absolute ethanol (150 ml), was then added with stirring at ambient temperature. Ethanol was removed by distillation. After the mixture was cooled to 50° C., pivaloylchloride (53 g, 0.4 mol) was added with stirring over a period of one hour and the resulting slurry stirred for a further hour. The mixture obtained was then filtered to remove sodium chloride and the filtrate added to dry sodium ethoxide, which had been prepared by dissolving sodium (9.29 g; 0.4 g at) in 250 ml of absolute ethanol and evaporating to dryness. After stirring for 90 minutes at 50° C., the mixture was acidified with dilute hydrochloric acid and the organic phase separated and dried over anhydrous magnesium sulphate. Evaporation of the solvent in a rotary evaporator followed by vacuum distillation afforded essentially pure ethyl pivaloylacetate product as a colorless liquid (b.p. 167° C. at 65 mbar). Structure of the product was confirmed with NMR analysis. The product yield, determined by GLC, was 0.343 mol (86%).

EXAMPLE 5

Preparation of methyl pivaloylacetate from dimethyl malonate was accomplished according to the following procedures. A 30 percent by weight solution of sodium methoxide in methanol (72 g solution, 0.4 mol of sodium methoxide) was added to a solution of dimethyl malonate (52.9 g, 0.4 mol) in di-sec-butyl ether (250 ml) with stirring at ambient temperature. Methanol was then distilled off. After temperature was lowered to 50° C., pivaloyl chloride (48.3 g, 0.4 mol) was added over a period of 30 minutes with vigorous stirring. The mixture was then stirred for a further 5 hours at 50° C. The product of the pivaloyl chloride reaction with the dimethyl malonate had a molar ratio of mono to di-pivaloyl derivative of 10:1 measured using GLC-analysis. The reaction mixture was then filtered to remove sodium chloride and the filtrate added to 0.4 mol of dry sodium methoxide (prepared by evaporating 72 g of 30 percent by weight sodium methoxide in methanol to dryness). The mixture of filtrate and sodium methoxide was then brought at 50° C. and stirred for 5 hours at that temperature. After acidification with dilute hydrochloric acid, the organic layer was separated and dried over anhydrous magnesium sulphate. GLC analysis of the dried organic phase indicated yield of methyl pivaloylacetate of 68%. Evaporation of the solvent in a rotary evaporator and distillation of the residue afforded essentially pure product as a colorless, mobile liquid (b.p. 110° C. at 100 mbar). The structure of the product was confirmed by NMR-analysis.

EXAMPLE 6

The procedures of Example 5 were again followed, with the exception of using cyclohexane as the solvent and introducing acetone (15 percent by weight, based on the reaction mixture) prior to the pivaloylation reaction involving the pivaloyl chloride. The degree of dipivaloylation was substantially decreased and the methyl pivaloylacetate product obtained in a yield of greater than 70 percent.

We claim as our invention:

1. A process for the preparation of alpha-pivaloyl-substituted acetic acid esters, which comprises steps for (a) reacting at a temperature in the range from about 15° to 100° C. a pivaloyl malonic acid ester of the formula

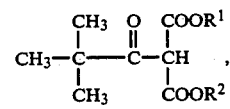

where $R^1$ and $R^2$ each individually represents an alkyl, aryl, alkaryl, or aralkyl group optionally substituted by one or more halogen atoms or alkoxy groups, with a base selected from the group consisting of alkali metal alkoxides and compounds of the formula MXY, wherein M is alkaline earth metal, X is an alkoxy group, and Y is either an alkoxy group or a halogen atom, and (b) acidifying the resulting reaction mixture.

2. The process of claim 1, wherein $R^1$ and $R^2$ each individually represents an alkyl group, and the base is an alkali metal alkoxide having an alkoxy group of less than six carbon atoms.

3. The process of claim 2, wherein $R^1$ and $R^2$ each individually represents a methyl or ethyl group, and the base is an alkali metal alkoxide having an alkoxy group of less than three carbon atoms.

4. The process of claim 3, wherein the pivaloyl malonic ester is reacted with the base in the presence of an organic solvent.

5. The process of claim 4, wherein the solvent is selected from the class consisting of aromatic hydrocarbons and dialkyl ethers.

6. The process of either claim 1, claim 3, or claim 5, wherein the pivaloyl malonic ester is reacted with the base at a temperature in the range of about 35° to 70° C.

7. A process for the preparation of alpha-pivaloyl-substituted acetic acid esters, which comprises steps for (a) converting a malonic acid ester of the formula $R^1OOCCH_2COOR^2$, wherein $R^1$ and $R^2$ each individually represents an alkyl, aryl, alkaryl, or aralkyl group optionally substituted by one or more halogen atoms or alkoxy groups, to a metal-diester salt, (b) reacting the metal diester salt with a pivaloyl halide to produce an alpha-pivaloyl-substituted malonic acid ester, (c) reacting at a temperature in the range from about 15° to 100° C. the alpha-pivaloyl-substituted malonic acid ester with a base selected from the group consisting of alkali metal alkoxides and compounds of the formula MXY, wherein M is an alkaline earth metal, X is an alkoxy group, and Y is either an alkoxy group or a halogen atom, and (d) acidifying the resulting reaction mixture from step (c).

8. The process of claim 7, wherein $R^1$ and $R^2$ each individually represent a methyl or ethyl group, the base is an alkali metal alkoxide having an alkoxy group of less than three carbon atoms, and steps (a), (b), (c), and (d) are carried out in an organic reaction solvent.

9. The process of claim 8, wherein steps (b), (c) and (d) are carried out in the presence of a di-alkyl ether solvent or a cycloalkane solvent.

10. A process for the preparation of alpha-pivaloyl-substituted acetic acid esters which comprises reacting at a temperature of from about 15°–100° C. a pivaloyl malonic acid ester of the formula

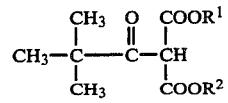

where $R^1$ and $R^2$ each individually represents an alkyl, aryl, alkaryl or aralkyl group optionally substituted by one or more halogen atoms or alkoxy groups, with an alkali metal alkoxide in the presence of a dialkyl ether solvent and acidifying the resultant reaction mixture.

* * * * *